United States Patent [19]
Dumoulin et al.

[11] Patent Number: 5,377,678
[45] Date of Patent: Jan. 3, 1995

[54] TRACKING SYSTEM TO FOLLOW THE POSITION AND ORIENTATION OF A DEVICE WITH RADIOFREQUENCY FIELDS

[75] Inventors: Charles L. Dumoulin, Ballston Lake; Robert D. Darrow, Scotia; John F. Schenck; Peter B. Roemer, both of Schenectady, all of N.Y.

[73] Assignee: General Electric Company, Schenectady, N.Y.

[21] Appl. No.: 91,419

[22] Filed: Jul. 14, 1993

Related U.S. Application Data

[63] Continuation of Ser. No. 753,563, Sep. 3, 1991, abandoned.

[51] Int. Cl.⁶ .......................... A61B 5/00; A61B 6/00
[52] U.S. Cl. ............................ 128/653.1; 128/653.2; 128/899; 378/63
[58] Field of Search ............ 128/653.1, 653.2, 653.5, 128/897, 898, 899; 378/63, 62

[56] References Cited

U.S. PATENT DOCUMENTS

| | | | |
|---|---|---|---|
| 3,847,157 | 11/1974 | Caillouette et al. | 128/653.1 |
| 4,173,228 | 11/1979 | Van Steenwyk et al. | 128/653.1 |
| 4,431,005 | 2/1984 | McCormick | 128/653.1 |
| 4,821,731 | 4/1989 | Martinelli et al. | 128/653.1 |
| 4,905,698 | 3/1990 | Strohl, Jr. et al. | 128/653.1 |
| 4,989,608 | 2/1991 | Ratner | 128/653.2 |
| 5,005,592 | 4/1991 | Cartmell | 128/653.1 |
| 5,042,486 | 8/1991 | Pfeiler et al. | 128/653.1 |
| 5,050,607 | 9/1991 | Bradley et al. | 128/653.5 |
| 5,078,140 | 1/1992 | Kwoh | 128/653.1 |
| 5,099,845 | 3/1992 | Besz et al. | 128/899 |
| 5,273,025 | 12/1993 | Sakiyama et al. | 128/899 |

FOREIGN PATENT DOCUMENTS

| | | | |
|---|---|---|---|
| 7703401 | 2/1977 | European Pat. Off. | |
| 0419729A | 9/1989 | European Pat. Off. | |
| 0362821 | 4/1990 | European Pat. Off. | 128/653.1 |
| 0399536 | 5/1990 | European Pat. Off. | |
| 2545349 | 11/1984 | France | 128/653.1 |

OTHER PUBLICATIONS

William H. Press, Brian P. Flannery, Saul A. Teukolsky, William T. Vetterling. "Numerical Recipes, The Art of Scientific Computing." Cambridge University Press, 1986, Chapt. 9—Newton–Raphson Method Using Derivatives, pp. 254–259.

*Primary Examiner*—Krista M. Pfaffle
*Attorney, Agent, or Firm*—Lawrence P. Zale; Marvin Snyder

[57] ABSTRACT

A tracking system in which radiofrequency signals emitted by an invasive device such as a catheter, are detected and used to measure the position and orientation of the invasive device. The invasive device has a transmit coil attached near its end and is driven by a low power RF source to produce a dipole electromagnetic field that can be detected by an array of receive coils distributed around a region of interest. The position and orientation of the device as determined by the tracking system are superimposed upon independently acquired Medical Diagnostic images, thereby minimizing the radiographic exposure times. One or more invasive devices can be simultaneously tracked.

18 Claims, 6 Drawing Sheets

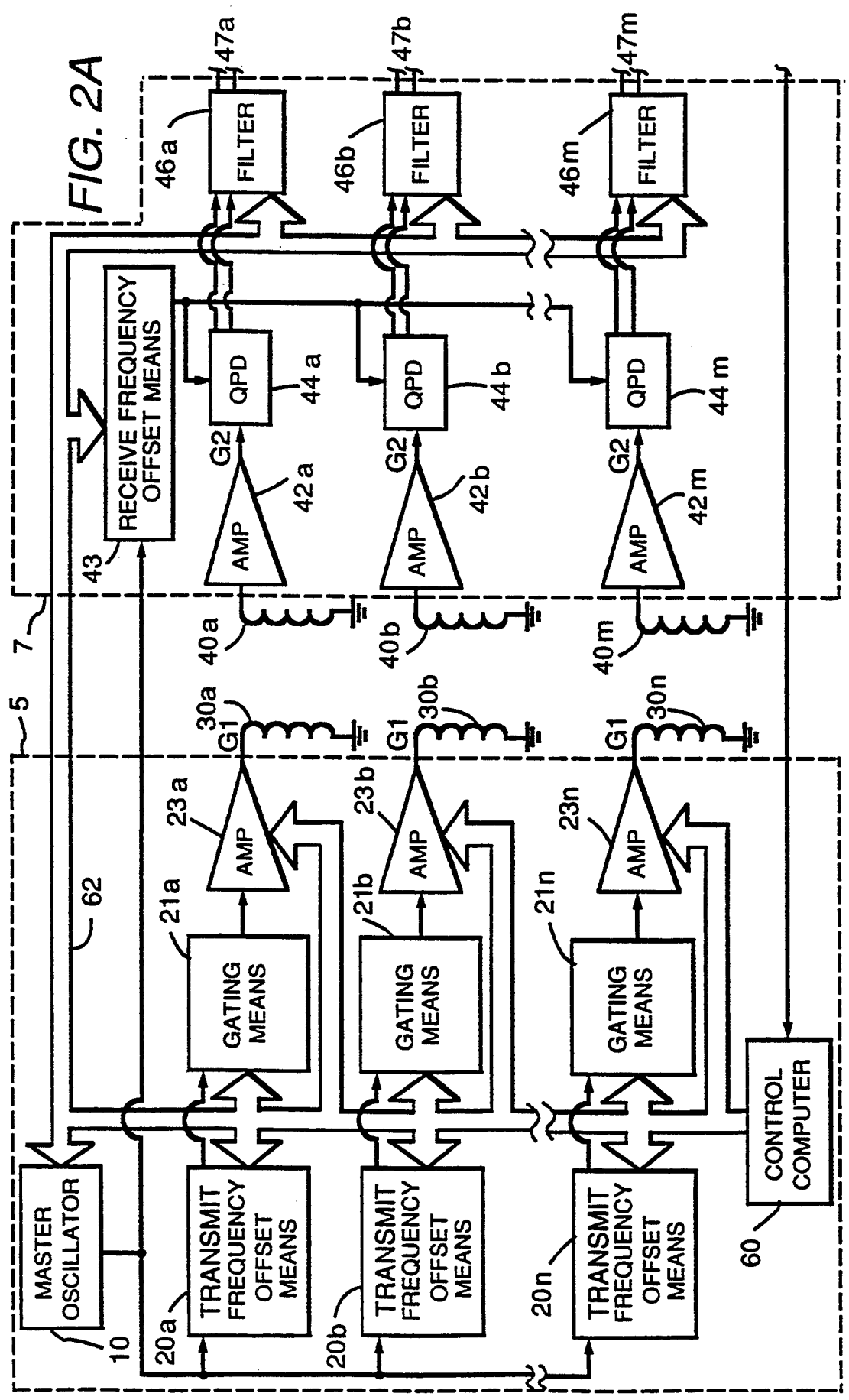

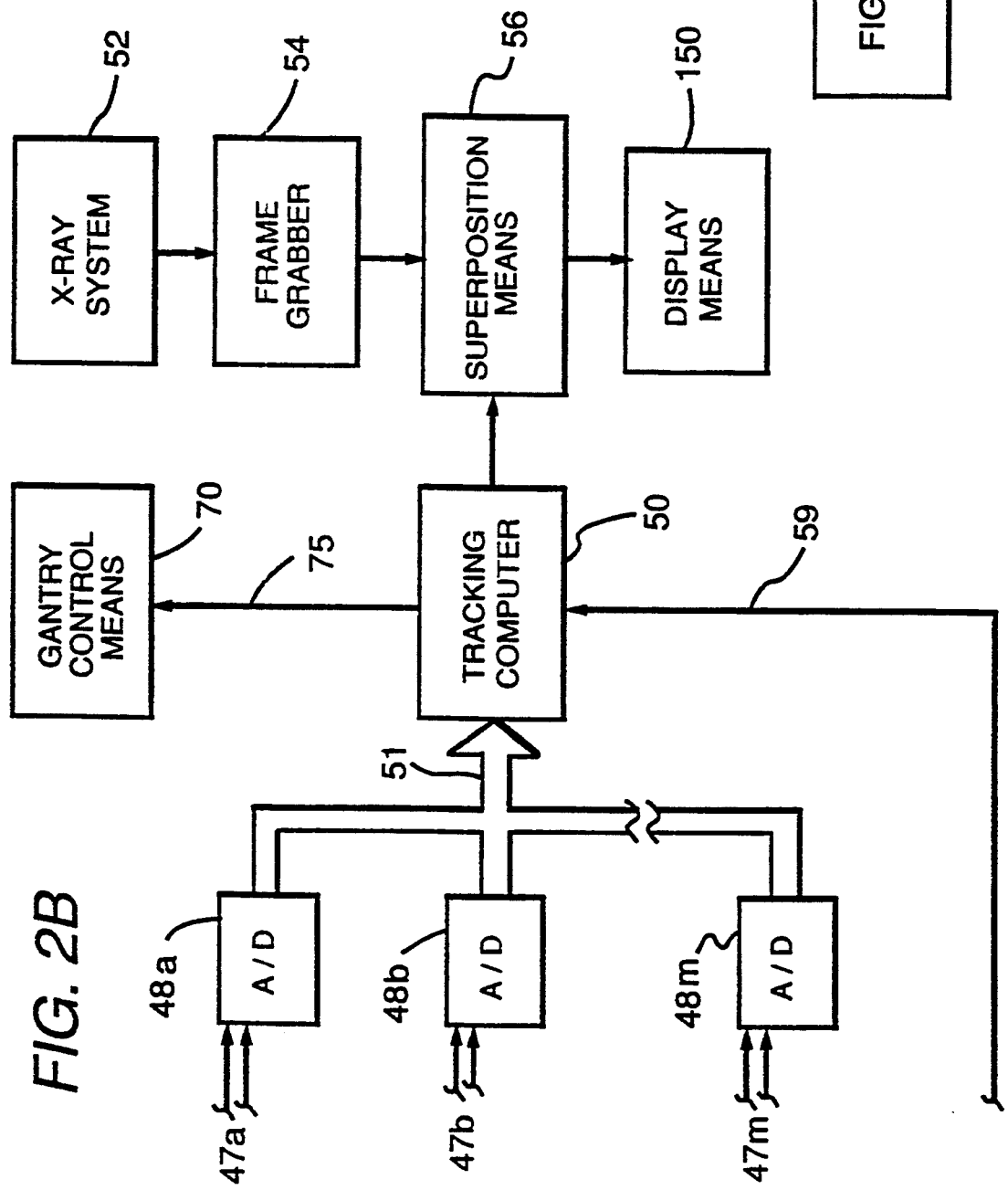

TRACKING SYSTEM TO FOLLOW THE POSITION AND ORIENTATION OF A DEVICE WITH RADIOFREQUENCY FIELDS

CROSS REFERENCE TO RELATED APPLICATIONS

This application is a continuation of application Ser. No. 07/753,563, filed Sep. 3, 1991, now abandoned.

This application is related to applications "Tracking System to Follow the Position and Orientation of a Device with Rradiofrequency Field Gradients", Ser. No. 07/753,565 filed Sep. 3, 1991, now U.S. Pat. No. 5,211,165; "Stereoscopic X-ray Fluoroscopy System Using Radiofrequency Fields" Ser. No. 07/753,564 filed Sep. 3, 1991, now U.S. Pat. No. 5,251,635; "Automatic Gantry Positioning for Imaging Systems" Ser. No. 07/753,567 filed Sep. 3, 1991, now U.S. Pat. No. 5,255,680; and "multi-planar X-ray Fluoroscopy System Using Radio Frequency Fields" Ser. No. 07/753,566, filed Sep. 3, 1991, now U.S. Pat. No. 5,265,610; all by Charles L. Dumoulin, all filed simultaneously with this application, and all assigned to the present assignee.

BACKGROUND OF THE INVENTION

The present invention relates to medical procedures in which an invasive device such as a catheter, guide wire, biopsy needle, endoscope, laparoscope or the like is inserted into a body, and more particularly concerns the tracking of such a device without the use of X-rays.

X-ray fluoroscopes are used routinely to monitor the placement of invasive devices during diagnostic and therapeutic medical procedures. Conventional X-ray fluoroscopes are designed to minimize X-ray dosage. Nevertheless, some procedures can be very long and the accumulated X-ray dose to the patient can become significant. The long term exposure of the attending medical staff is of even greater concern since they participate in these procedures regularly. Consequently, it is desirable to reduce the X-ray dose during these procedures.

Another limitation on the use of X-ray fluoroscopes is that the technique is projective in nature and produces a single two-dimensional image. Information concerning the depth of an object within the field-of-view is not available to the operator. It is often desirable to obtain this information during invasive procedures.

SUMMARY OF THE INVENTION

Tracking of catheters and other invasive devices without X-rays is accomplished using RF transmitters and receivers. An invasive device such as a guide wire, catheter, endoscope, laparoscope or biopsy needle is modified by attaching a small transmit coil near its end. This transmit coil is driven by a low power RF source and creates a dipole electromagnetic field. This dipole field induces currents and voltages in an array of receive coils distributed around a region of interest. These voltage signals from the receive coils are digitized and sent to a tracking computer for analysis. The tracking computer utilizes non-linear iterative methods to solve for the position and orientation of the transmit coil. This positional information is then superimposed on a video image of the region of interest. Simultaneous detection of multiple transmit coils to better characterize the position and orientation of the invasive device can be accomplished using both time and frequency multiplexing schemes.

OBJECTS OF THE INVENTION

It is an object of the present invention to provide a system for tracking an invasive device without using X-rays.

It is another object of the present invention to provide a method of tracking an invasive device which minimizes any X-ray dose to the patient and medical staff.

It is another object of the present invention to provide an interactive image of an invasive device superimposed upon another medical diagnostic image.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

FIGS. 2A and 2B together are a schematic block diagram of a radiofrequency tracking system according to the present invention.

FIG. 2C is a diagram illustrating how FIGS. 2A and 2B are assembled.

DETAILED DESCRIPTION OF THE INVENTION

Figure 1:
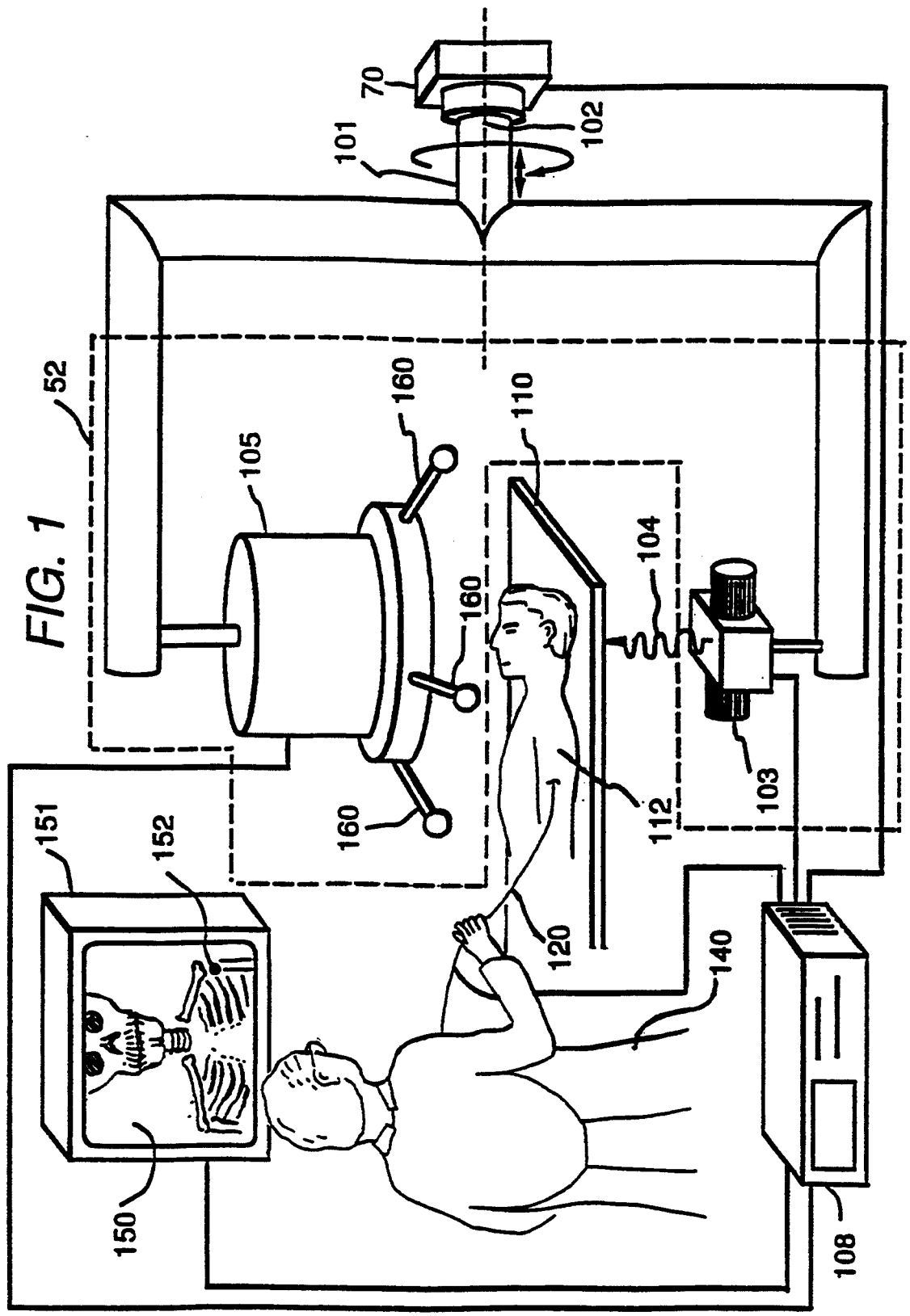
FIG. 1 is a perspective view of one embodiment of the present invention in operation tracking the location and orientation of an invasive device in a patient.

In FIG. 1, a support arm 101 capable of being rotating about at least one axis 102 and translated by gantry control means 70 is shown. Support arm 101 holds an X-ray source 103 that emits a substantially collimated beam of X-rays 104 suitable for X-ray imaging and X-ray fluoroscopy. Support arm 101 also holds an X-ray detection means 105 aligned with the propagation direction of X-rays 104 emitted by X-ray source 103. X-rays 104 penetrate a subject support table 110 and a subject 112. An invasive device 120 is placed inside the subject by an operator 140. The location of the invasive device 120 is visible on the display of an X-ray image on a display monitor 151 of display means 150 driven by a tracking/display unit 108. In fluoroscopic usage, this image is acquired and displayed several (12 to 60) times a second.

According to the invention, a plurality of M RF receive coils 160 are placed about the subject. In the preferred embodiment, receive coils 160 are attached to X-ray detection means 105. Invasive device 120 is modified to incorporate a small RF transmit coil (not shown in FIG. 1). The transmit coils may be attached to several invasive devices, with at least one coil per invasive device to determine its position and at least two coils per invasive device to determine its orientation. Tracking/display unit 108 provides power to the RF transmit coil to create a dipole electromagnetic field which is detected by RF receive coils 160. The signals detected by receive coils 160 are used by tracking/display unit 108 to calculate the position and orientation of the transmit coil (and therefore invasive device 120). The calculated position of invasive device 120 is displayed by superposition of a symbol 152 on an X-ray image appearing on video monitor 151.

Following the preferred procedure, operator 140 initiates acquisition of X-ray image only when it is deemed necessary, in order to minimize X-ray dose to subject 112 and operator 140. The instantaneous location of invasive device 120 is updated several times per second (ideally 12 to 60 times per second) and provides an approximation of the fluoroscopic image of invasive device 120 that operator 140 would expect to see with a conventional X-ray fluoroscopic system.

Tracking/display unit 108 is comprised of an RF transmitter 5 and an RF receiver 7 as shown in FIG. 2A, and analog-to-digital (A/D) converters 48a, 48b, 48m, a tracking computer 50, a frame grabber 54, and a superposition means 56 as shown in FIG. 2B. RF transmitter 5 employs a master oscillator 10 that generates a signal at a selected frequency. This signal is propagated to a plurality of N frequency offset means 20a, 20b, 20n which generate a plurality N signals of selected different frequencies. Each frequency offset means 20a, 20b, 20n propagates its signal to a gating means 21a, 21b, 21n, respectively, which either passes the signal to an amplifier means 23a, 23b, 23n, respectively, or blocks the signal. Amplifier means 23a, 23b, 23n boost the signals by a selected gain G1 and drive transmit coils 30a, 30b, 30n, respectively. In the preferred embodiment, a number N of these transmit coils 30a, 30b, 30n are situated on invasive device 120.

The signals generated by the transmit coils are detected by a plurality of M receive coils 40a, 40b, 40m placed at known locations and with known orientation about the subject. Each receive coil 40a, 40b, 40m detects signals emitted by all transmit coils. The amplitudes and phases of these detected signals are a function of the relative placement and orientations of the transmit and receive coils. The signals detected by each receive coil 40a, 40b, 40m are propagated to low-noise amplifiers 42a, 42b, 42m, respectively, in RF receiver 7, where they are amplified by a selected gain factor G2. The amplified signals are passed from low-noise amplifiers 42a, 42b, 42m to quadrature phase detectors 44a, 44b, 44m, respectively, where they are mixed with a reference signal from a receive frequency offset means 43 that is driven by master oscillator 10. Mixing two signals in each quadrature phase detector results in a signal having a component at a frequency equal to the sum of the input frequencies, and a component at a frequency equal to the difference of the input frequencies. The component of interest in the preferred embodiment of this invention is the component equal to the difference of the input frequencies. The signals are propagated in quadrature fashion (i.e. as pairs of signals having a 90 degree phase difference) to filters 46a, 46b, 46m, respectively, where the low frequency component is selected and propagated to A/D converters 48a, 48b, 48m, respectively. The A/D converters convert the low frequency signals in each quadrature pair to digital form. This digital information is sent to tracking computer 50 through a data bus 51. The tracking computer calculates the positions and orientations of the N transmit coils using the digitized signals derived from the M receive coils. The calculated positions and orientations of the N transmit coils are transformed to display coordinates.

X-ray imaging and fluoroscopy system 52 is used to generate a video signal that is propagated to frame grabber means 54 which captures a single image from X-ray system 52. Frame grabber means 54 propagates the single X-ray image in video form to superposition means 56 which overlays a symbol 152 on the video signal supplied by frame grabber means 54. The composite video signal is propagated to a suitable display means 150 such as video monitor 151 shown in FIG. 1. The X-ray image will detect the invasive device. The tracking computer 50 is initialized by placing the invasive device at an origin marked on the table 110, and setting the position to zero. The X-ray system, likewise is adjusted to coincide with the origin marked on the table.

Tracking computer 50 communicates with a control computer 60 (FIG. 2A) through an interface connection 59. Control computer 60 is also interfaced through a control bus 62 to transmit frequency offset means 20a, 20b, 20n, gating means 21a, 21b, 21n, transmitter amplifier means 23a, 23b, 23n, receive frequency offset means 43, and filters 46a, 46b, 46m. Furthermore, tracking computer 50 is interfaced through an interface connection 75 to a gantry control means 70 which is capable of changing the relative position and orientation of the subject and the x-ray detection means 105 (FIG. 1). Control computer 60 is responsive to a timing signal from master oscillator 10.

In the preferred embodiment of this invention transmit coils 30a, 30b, 30n are placed on invasive device 120 illustrated in FIG. 1. Reciprocity between receive and transmit coils exists, and placement of receive coils 40a, 40b, 40m on invasive device 120 and placement of transmit coils 30a, 30b, 30n outside the subject is possible.

In the illustrated embodiment of the invention, a minimum of N=1 transmit coils and M=5 receive coils is required to unambiguously determine the location and orientation of invasive device 120. It can be advantageous, however, to have N>1 transmit coils to provide location and orientation for multiple points on the invasive device and/or multiple invasive devices.

Several methods for detecting signals from multiple transmit coils are possible. One method requires that only one of the N gating means be allowed to propagate signal at any instant. Selection of the propagating gating means is made by control computer 60. Control computer 60 notifies tracking computer 50 of a gating means selected. The process is repeated for each of the N coils. Thus, tracking computer 60 is able to calculate the position of N transmit coils.

An alternative embodiment requires that all N transmit coils be active at once, each transmitting at a different frequency. If all N transmit frequencies are within the selected bandwidth of each filter means, then a collection of L data points can be acquired from each A/D converter means. The data points are demultiplexed by Fourier or Hadamard transformation to separate the individual frequency components arising from each transmit coil. Alternatively, M receivers can be constructed for the N transmitters if each transmit frequency is within a bandwidth of the filter means of the M receivers.

Figure 3:
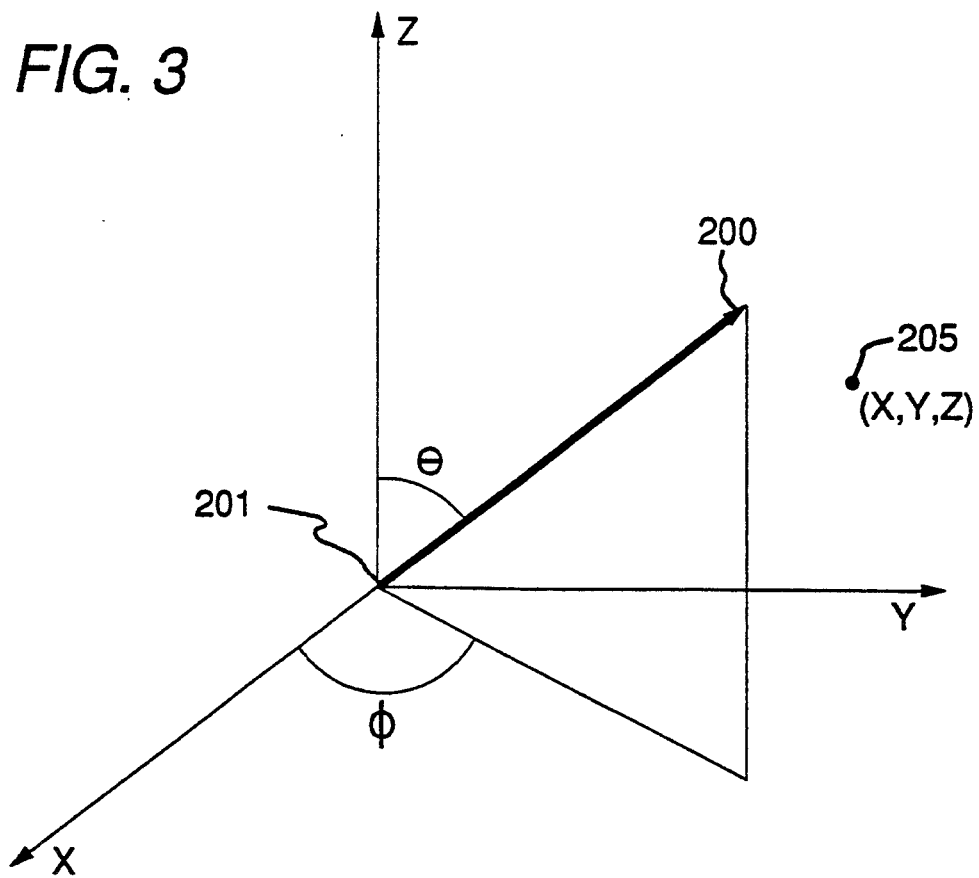
FIG. 3 is a vector representation of an electromagnetic dipole located at the origin.

Turning now to FIG. 3 a vector representation of an electromagnetic dipole 200 located in a three-dimensional coordinate system comprising an X axis, Y axis and Z axis, and having an origin 201, is shown. The strength of the electromagnetic field generated by the dipole at a given position (given as x, y and z) in three-dimensional space is a function of position 205, the orientation of the dipole, here defined by rotation angles $\theta$ and $\phi$ and the physical constant $\mu_o$ known as the permeability of free space, and can be expressed as:

$$B(x,y,z) = \quad [1]$$

$$\frac{\mu_o}{4\pi R^5} [(M_x(2x^2 - z^2 - y^2) + 3 M_y x y + 3 M_z xz)\hat{i} +$$

$$(M_y(2y^2 - x^2 - z^2) + 3 M_x x y + 3 M_z yz)\hat{j} +$$

$$(M_z(2z^2 - x^2 - y^2) + 3 M_x x z + 3 M_y zy)\hat{k}]$$

In this equation the electromagnetic field at a selected position 205 in space is divided into three orthogonal components defined by the unit vector quantities i, j and k. R represents the distance between the location of the dipole and the selected position, and is defined as:

$$R = \sqrt{x^2 + y^2 + z^2} \quad [2]$$

The quantities $M_x$, $M_y$ and $M_z$ represent the vector components of the unit dipole along the x, y and z axes and can be expressed as:

$$M_z = \cos(\theta) \quad [3]$$

$$M_y = \sin(\phi)\sin(\theta) \quad [4]$$

$$M_x = \cos(\phi)\sin(\theta) \quad [5]$$

where $\theta$ and $\phi$ are the angles shown in FIG. 3.

Figure 4:
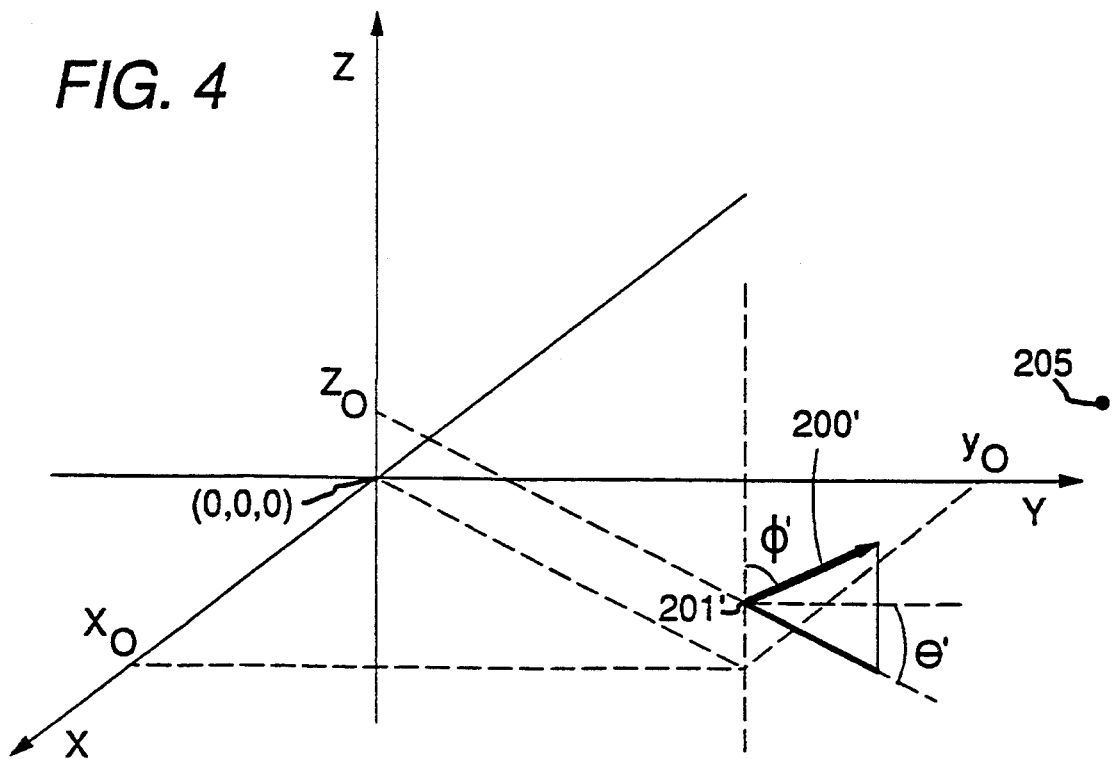
FIG. 4 is a vector representation of an electromagnetic dipole located at a position in space other than the origin.

In the present invention it is convenient to translate the location of the dipole to a position other than the origin, as illustrated in FIG. 4. Since the coordinate system is simply translated and not rotated, the rotation angles in the new coordinate system $\theta'$ and $\phi'$ are identical to the original rotation angles $\theta$ and $\phi$. The translated origin is 201' ($x_0$, $y_0$, $z_0$). The translated dipole 200' creates an electromagnetic field at a selected receive coil, i, in space at position 205 ($x_i$, $y_i$, $z_i$) which can be calculated from equation 1 using the following substitutions for x, y and z:

$$x = x_i - x_0 \quad [6]$$

$$y = y_i - y_0 \quad [7]$$

$$z = z_i - z_0 \quad [8]$$

Each receive coil is positioned at a predetermined location, with receive coil 1 being located at ($x_1$, $y_1$, $z_1$), receive coil 2 at ($x_2$, $y_2$, $z_2$), etc. Receive coil 1 experiences an electromagnetic field of flux density $B_1$ at location ($x_1$, $y_1$, $z_1$) from the transmit coil transmitting from point ($x_0$, $y_0$, $z_0$), translated from the origin.

The same transmit coil at the same point ($x_0$, $y_0$, $z_0$), causes receive coil 2 to experience a magnetic field of flux density $B_2$ at a location ($x_2$, $y_2$, $z_2$). This is true for all receive coils at a given instant.

Since $x = x_i - x_0$, $y = y_i - y_0$, and $z = z_i - z_0$, x, y and z in equation 1 can be replaced by known quantities resulting in:

$$B_i(x_i, y_i, z_i) = \quad [9]$$

$$\frac{\mu_o}{4\pi R^5} [<(M_x\{2(x_i - x_0)^2 - (z_i - z_0)^2 - (y_i - y_0)^2\} +$$

$$3 M_y(x_i - x_0)(y_i - y_0) + 3 M_z(x_i - x_0)(z_i - z_0)> \hat{i} +$$

$$<M_y\{2(y_i - y_0)^2 - (x_i - x_0)^2 - (z_i - z_0)^2\} +$$

$$3 M_x(x_i - x_0)(y_i - y_0) + 3 M_z(y_i - y_0)(z_i - z_0)> \hat{j} +$$

$$<(M_z\{2(z_i - z_0)^2 - (x_i - x_0)^2 - (y_i - y_0)^2\} +$$

$$3 M_x(x_i - x_0)(z_i - z_0) + 3 M_y(z_i - z_0)(y_i - y_0)> \hat{k}]$$

for each of i=1 to M receive coils. These equations can be generalized as:

$$B_1 = f(\theta, \phi, x_0, y_0, z_0)$$
$$B_2 = f(\theta, \phi, x_0, y_0, z_0)$$
$$B_3 = f(\theta, \phi, x_0, y_0, z_0)$$
$$B_4 = f(\theta, \phi, x_0, y_0, z_0)$$
$$\cdot$$
$$\cdot$$
$$\cdot$$
$$B_m = f(\theta, \phi, x_0, y_0, z_0)$$

which is a set of M equations with 5 unknowns. These equations are solvable provided $M \geq 5$, meaning that there must be at least 5 receive coils.

Figure 5:
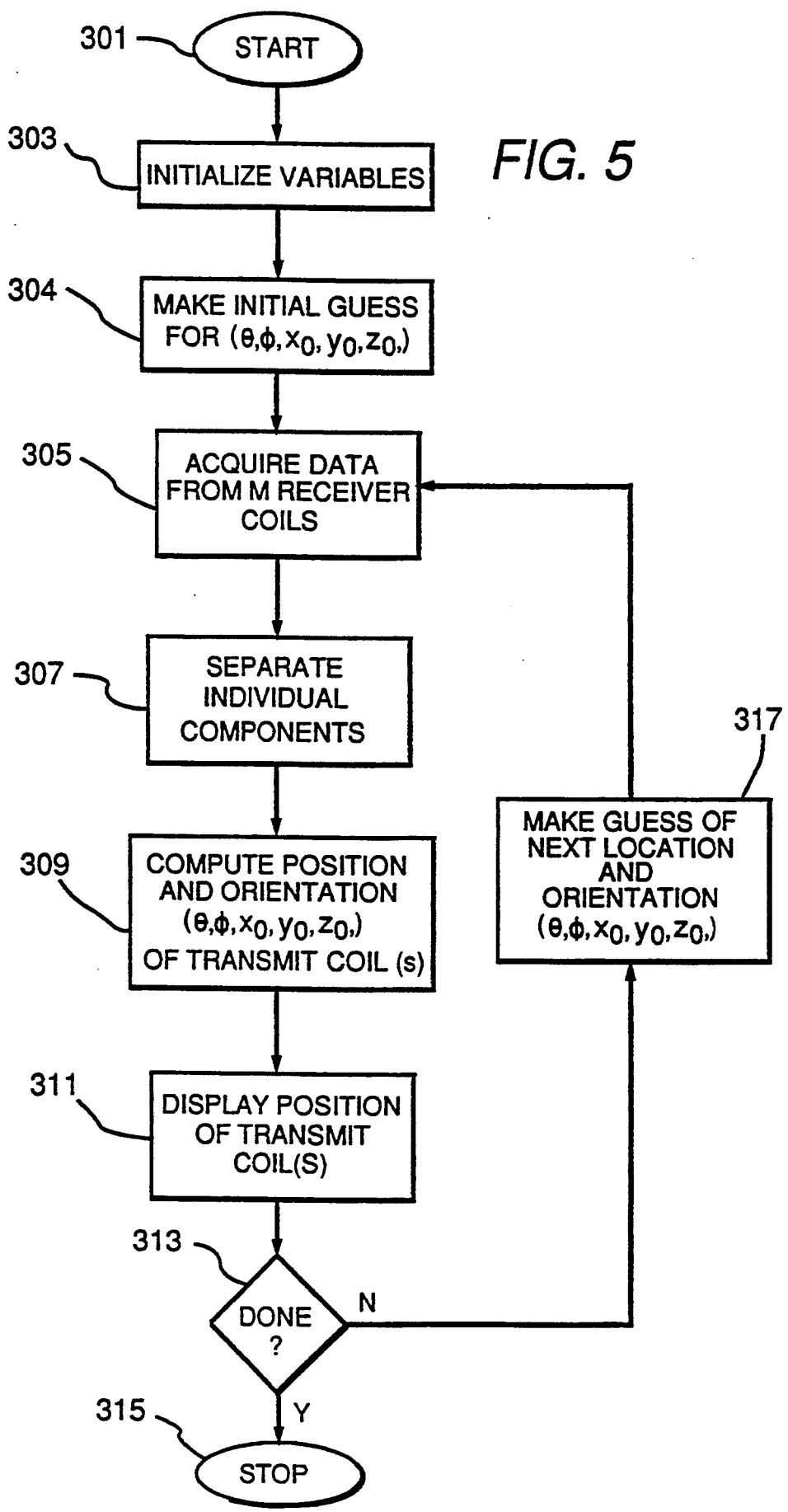
FIG. 5 is a flowchart of the method used to compute the position and orientation of an invasive device.

Tracking computer 50 (FIG. 2B) is used to solve the (x, y, z) position data for the transmit coils acting as a dipole. A flow diagram of a method of solving for the position data is shown in FIG. 5. Step 301 serves as the entry into the method. Step 303 initializes variables to appropriate values.

Step 304 provides an initial guess for the location and orientation ($\theta$, $\phi$, $x_0$, $y_0$, $z_0$) of the N transmit coils being tracked. This initial guess is obtained by placing the invasive device at a predetermined position which is marked on table 110 (FIG. 1) as being ($x_0, y_0, z_0$) location, and aligning the invasive device at a predetermined orientation ($\theta$, $\phi$) also marked on the table at the beginning of the tracking process.

At step 305, data are acquired from the M receive coils. At step 307, the N components contained in each of the M sets of data acquired by the receive coils are separated. This separation can be accomplished by Fourier or Hadamard transformation or any other appropriate methods. At step 309, the position of each of the N transmit coils is computed by using equation [9]. Step 309 can be performed by any suitable mathematical algorithm, although our preferred method is an iterative non-linear optimization such as a multi-dimensional Newton-Raphson procedure as explained in *Numerical Recipes, The Art of Scientific Computing*, by William H. Press, Brian P Flannery, Saul A. Teukolsky and William T. Vetterling, Cambridge University Press, 1986, chapter 9.4 "Newton-Raphson Method Using Derivatives" hereby incorporated by reference. The Newton-Raphson procedure is applied to minimize the difference between the data acquired from the M receive coils and the predicted data calculated by using equations [1–9] for the best guess of the N transmit coil positions ($x_0,y_0,z_0$) and orientations ($\theta,\phi$). At step 311 of the algorithm, the calculated position ($x_0,y_0,z_0$) of the N transmit coils 30a, 30b, 30n is displayed by the superposition means 56 and display means 150 (FIG. 2B). Step 313 of the algorithm determines whether the tracking process is complete. If the tracking process is complete, step 315 of the algorithm is taken and the process stops; otherwise, a new guess of the position $(x_0,y_0,z_0)$ and orientation $(\theta,\phi)$ for each of the N transmit coils is made at step 317 of the algorithm. The presently preferred method to make the guess at step 317 is a linear extrapolation of the position and orientation based on the two immediately prior positions and orientations calculated for each of the N coils. After step 317 of the algorithm is complete, the process continues with acquisition of new data at step 305.

Referring now to FIG. 1, the present invention is also concerned with the automatic placement and alignment of the subject, by use of a support arm 101, within a desired region around invasive device 120. This is accomplished in the present instance by transferring the calculated position of the invasive device from tracking computer 50 (FIG. 2B) to a means 70 for controlling the position and orientation of support arm 101 in relation to support table 110. An X-ray image can be also initiated whenever invasive device 120 enters a region of the subject for which an additional X-ray image is required. This embodiment frees the operator from the task of keeping the invasive device 120 within the field-of-view of the X-ray system 52 and potentially reduces the number of assistants that the operator requires.

Figure 6:
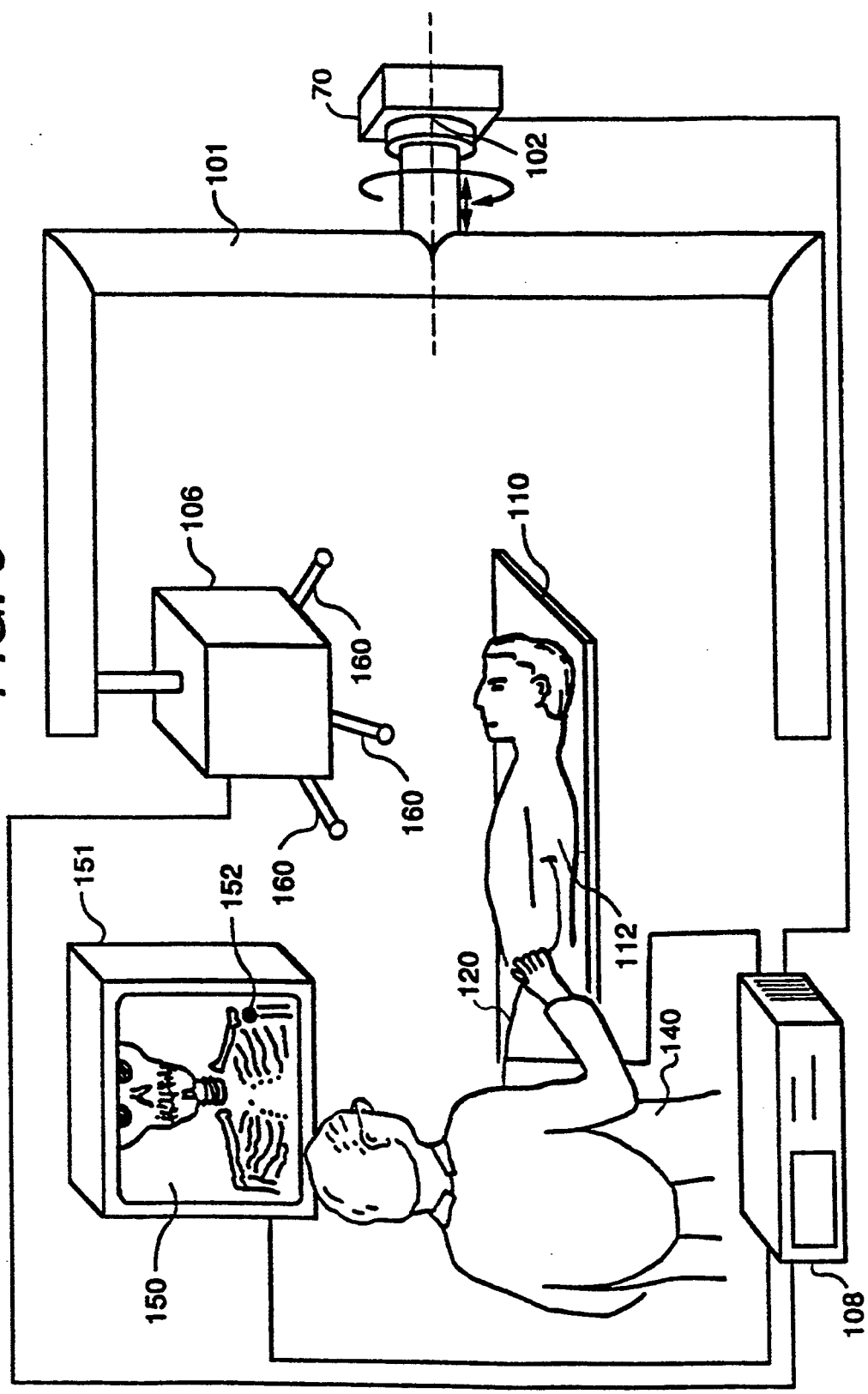
FIG. 6 is a perspective view of another embodiment of the present invention employing alternate imaging means.

Radiologic images upon which the symbol representing the invasive device is superimposed may be obtained by means other than X-rays. Data obtained with Magnetic Resonance scanners, Ultrasound scanners, Positron Emission Tomography scanners and the like shown as an imaging means 106 of FIG. 6 can be used in place of X-ray system 52.

While several presently preferred embodiments of the novel radiofrequency tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A tracking and imaging system for following a position and orientation of at least one invasive device within a subject, comprising:
   a) an invasive device;
   b) an electromagnetic (EM) creation means attached to the invasive device, for creating an electromagnetic field of known geometry, and known electromagnetic flux defined by a plurality of known electromagnetic field vectors within the subject, EM field creation means comprising:
      i. a master oscillator for setting a standard timing signal;
      ii. a control computer coupled to the master oscillator and responsive to the standard timing signal; and
      iii. a plurality of N transmit branches, wherein $N \geq 1$, each of the transmit branches comprises:
         A. transmit frequency offset means for creating an RF transmit signal of a frequency determined by the control computer based upon the standard timing signal,
         B. a gating means coupled to the transmit frequency offset means and responsive to the control computer adapted for selectively passing or not passing the RF transmit signal,
         C. an amplifier responsive to the control computer for receiving the RF transmit signal from the gating means and amplifying the RF transmit signal with a gain determined by the control computer, and
         D. a transmit coil coupled to the amplifier for creating the electromagnetic field of known geometry from the RF transmit signal;
   c) a radiofrequency (RF) receiver for detecting the electromagnetic field vector at a plurality of M greater than 5 selected locations;
   d) imaging means for acquiring a medical diagnostic image; and
   e) a tracking means for computing a position and an orientation relative to the acquired medical diagnostic image of the EM field creation means being substantially said position and said orientation of the invasive device, the tracking means being responsive to the electromagnetic field vectors detected by the RF receiver at the M selected locations.

2. The tracking and imaging system of claim 1 further comprising:
   a) superposition means for superimposing a symbol at the computed position representing the EM field creation means on the medical diagnostic image resulting in a superimposed image; and
   b) display means adapted for displaying the superimposed image.

3. The tracking and imaging system of claim 2, wherein the imaging means comprises an X-ray imaging system.

4. The tracking and imaging system of claim 3, wherein said X-ray system includes means for providing a selected X-ray image from a fluoroscopic sequence as the medical diagnostic image.

5. The tracking and imaging system of claim 2, wherein the imaging means comprises a Magnetic Resonance imaging system.

6. The tracking imaging system of claim 2, wherein the imaging means comprises a Position Emission Tomography imaging system.

7. The tracking and imaging system of claim 1, wherein the EM field creation means comprises means for generating an electromagnetic dipole.

8. The tracking and imaging system of claim 1, wherein the invasive device is one of the group consisting of a guide wire, a catheter, an endoscope, a laparoscope, and a biopsy needle.

9. The tracking and imaging system of claim 1, wherein the invasive device is a surgical device.

10. The tracking and imaging system of claim 1, wherein the invasive device is a therapeutic device.

11. The tracking and imaging system of claim 1, wherein the RF receiver comprises:
    a) receive frequency offset means for generating a reference frequency signal; and
    b) a plurality of M receive branches, each of the receive branches comprising:
       i. a receive coil for sensing the electromagnetic field,
       ii. an amplifier coupled to the receive coil for producing an amplified signal in response to said receive coil sensing said electromagnetic field,
       iii. a quadrature phase detector coupled to the amplifier and the receive frequency offset means for sampling the amplified signal to create a sampled signal having high frequency components and low frequency components, and comparing the sampled signal to the reference frequency signal, iv. a filter for filtering out the high frequency components and passing the low frequency component of the sampled signal, and v. an A/D converter coupled to the filter for creating a digital signal representing the electromagnetic field within the subject as detected by the receive coil.

12. The tracking and imaging system of claim 11, wherein the filter further includes means for permitting the M receive branches to simultaneously detect N electromagnetic fields for computing N positions and orientations.

13. The tracking and imaging system of claim 12, wherein the tracking means incorporates a demultiplexing algorithm comprising one of the group consisting of a Fourier transform and a Hadamard transform.

14. The tracking and imaging system of claim 1, wherein the gating means is for permitting only a selected one of the N transmit branches to create an electromagnetic field at any given instant in time.

15. The tracking and imaging system of claim 1, including means for permitting the N transmit branches to simultaneously create N electromagnetic fields for detection by the RF receiver, said tracking means being responsive to said N electromagnetic fields for computing N positions and orientations.

16. The tracking and imaging system of claim 1, wherein the EM field creation means for permitting a plurality of the transmit branches to create electromagnetic fields of different RF frequencies at a given instant, and the RF receiver is for detecting the electromagnetic fields of different RF frequencies.

17. A tracking system and imaging system for following a location of at least one invasive device within a subject, comprising:
a) an invasive device;
b) an electromagnetic (EM) creation means for creating an electromagnetic field of known geometry within the subject, the EM field creation means comprising:
i. a master oscillator for setting a standard timing signal;
ii. a control computer coupled to the master oscillator and responsive to the standard timing signal; and
iii. a plurality of N transmit branches, wherein $N \geq 1$, each of the transmit branches comprises:
A. transmit frequency offset means for creating an RF transmit signal of a frequency determined by the control computer based upon the standard timing signal,
B. a gating means coupled to the transmit frequency offset means and responsive to the control computer for selectively passing or not passing the RF transmit signal,
C. an amplifier responsive to the control computer for receiving the RF transmit signal from the gating means and amplifying the RF transmit signal with a gain determined by the control computer, and
D. a transmit coil coupled to the amplifier for creating the electromagnetic field of known geometry from the RF transmit signal;

c) a radiofrequency (RF) receiver attached to the invasive device for detecting the electromagnetic field at a plurality of M selected locations;
d) imaging means for acquiring a medical diagnostic image; and
e) a tracking means for computing a position and an orientation relative to the acquired medical diagnostic image of the EM field creation means at the M selected locations indicating the location of the invasive device, the tracking means being responsive to the detected electromagnetic field.

18. A tracking system adapted and imaging system for following a position and an orientation of a plurality of invasive devices within a subject, comprising:
a) a plurality of invasive devices;
b) a plurality of electromagnetic (EM) creation means with at least one attached to each invasive device, for creating an electromagnetic field of known geometry, and known electromagnetic flux defined by a plurality of known electromagnetic field vectors within the subject, comprising:
i. a master oscillator for setting a standard timing signal;
ii. a control computer coupled to the master oscillator and responsive to the standard timing signal; and
iii. a plurality of N transmit branches, wherein $N \geq 1$, each of the transmit branches comprises:
A. transmit frequency offset means for creating an RF transmit signal of a frequency determined by the control computer based upon the standard timing signal,
B. a gating means coupled to the transmit frequency offset means and responsive to the control computer for selectively passing or not passing the RF transmit signal,
C. an amplifier responsive to the control computer for receiving the RF transmit signal from the gating means and amplifying the RF transmit signal with a gain determined by the control computer, and
D. a transmit coil coupled to the amplifier for creating the electromagnetic field of known geometry from the RF transmit signal;

c) a radiofrequency (RF) receiver for detecting the electromagnetic field vectors at a plurality of M greater than 5 selected locations;
d) imaging means for acquiring a medical diagnostic image; and
e) a tracking means for computing a position and an orientation of each EM field creation means relative to the acquired medical diagnostic image being substantially the position and the orientation of each invasive device, the tracking means being responsive to the electromagnetic field vectors detected by the RF receiver at the M selected locations.

* * * * *